United States Patent [19]

Guzman et al.

[11] Patent Number: 5,354,277

[45] Date of Patent: Oct. 11, 1994

[54] SPECIALIZED PERFUSION PROTOCOL FOR WHOLE-BODY HYPERTHERMIA

[75] Inventors: Joseph A. Guzman, Atlanta, Ga.; Miguel P. Cosio, Piso, Mexico

[73] Assignee: Biocontrol Technology, Inc., Pittsburgh, Pa.

[21] Appl. No.: 940,546

[22] Filed: Sep. 4, 1992

[51] Int. Cl.$^5$ .............................................. A61M 1/03
[52] U.S. Cl. ....................................... 604/113; 604/4; 604/6
[58] Field of Search ................... 604/4, 5, 6, 113, 114, 604/19, 27, 28

[56] References Cited

U.S. PATENT DOCUMENTS

| | | | |
|---|---|---|---|
| 2,886,771 | 5/1959 | Vincent | 324/30 |
| 3,482,575 | 12/1969 | Claff et al. | 128/214 |
| 4,061,141 | 12/1977 | Hyden et al. | 128/214 |
| 4,191,182 | 3/1980 | Popovich et al. | 128/214 |
| 4,321,918 | 3/1982 | Clark, II | 128/214 |
| 4,322,275 | 3/1982 | Jain | 204/180 |
| 4,381,004 | 4/1983 | Babb | 128/214 |
| 4,479,798 | 10/1984 | Parks | 604/175 |
| 4,540,401 | 9/1985 | Marten | 604/28 |
| 4,563,170 | 1/1986 | Aigner | 604/5 |
| 4,576,143 | 3/1986 | Clark, III | 128/1 |
| 4,692,138 | 8/1987 | Troutner et al. | 604/4 |
| 4,787,883 | 11/1988 | Kroyer | 604/4 |
| 4,808,159 | 2/1989 | Wilson | 604/4 |
| 4,950,225 | 8/1990 | Davidner et al. | 604/4 |

OTHER PUBLICATIONS

DeMoss, J. L. et al., "Hyperthermia in the Treatment of Cancer," The Journal of Extra-Corporeal Technology, vol. 17, No. 1, pp. 37-43 (1985).

Sanchez, R. et al., "Overview of Whole Body Hyperthermia Experience at American International Hospital," Consensus on Hyperthermia for the 1990s, Plenum Press, New York, pp. 203-308 (1990).

Levin, R. D. et al., "Whole Body Hyperthermia Experience in Breast Cancer at American International Hospital," Consensus on Hyperthermia for the 1990s, Plenum Press, New York, pp. 387-391 (1990).

Perez, C. A. et al., "Randomized Phase III Study Comparing Irradiation and Hyperthermia with Irradiation Alone in Superficial Measurable Tumors",: Am. J. Clin. Oncol., vol. 14, No. 2, pp. 133-141 (1991).

O'Malley S., "Hyperthermia Perfusion's Answer . . . ?", Perfusion Life, pp. 6-13 (1991).

Logan, W. D. et al., "Case Report: Total Body Hyperthermia in the Treatment of Kaposi's Sarcoma . . . ", Med. Oncol. & Tumor Pharmacother, vol. 8, No. 1, pp. 45-47 (1991).

AIDS Treatment News, Issue No., 104, p. 2 (1990).

Weatherburn, H., "Hyperthermia . . . ," The British Journal of Radiology, vol. 61, No. 729, pp. 863-864 (1988).

Yatvin, M. B., "An Approach . . . Using Hyperthermia and Membrane Modification," Medical Hypotheses, vol. 27, pp. 163 $\propto$ 165 (1988).

*Primary Examiner*—Robert A. Hafer
*Assistant Examiner*—Sam Rimell
*Attorney, Agent, or Firm*—Webb Ziesenheim Bruening Logsdon Orkin & Hanson

[57] ABSTRACT

A method for extracorporeal blood treatment which utilizes a hemodialysis machine capable of heating the dialysis fluids to 48° C., a hollow-fiber, high efficiency hemodialyzer, and a tubular heat exchanger—in addition to various probes and catheters and heated anterior and posterior blankets for the patient—to effect extracorporeal treatment without adverse effect on blood physiology and without the need for general anesthesia.

18 Claims, No Drawings

SPECIALIZED PERFUSION PROTOCOL FOR WHOLE-BODY HYPERTHERMIA

FIELD OF THE INVENTION

The present invention relates to a specialized method for whole-body hyperthermia, including extracorporeal blood heating and dialysis, as an antiviral protocol.

BACKGROUND OF THE INVENTION

Hyperthermia as a treatment of tumors has been carefully studied and applied since the 1960's. Prior to that period there were multiple reports of tumor regression coincident with episodes of fever. Biochemical analysis of the effects of hyperthermia has indicated that temperatures greater than 41° C. generally are needed to induce tumor necrosis (tumor death). Although there are multiple methods of inducing hyperthermia including paraffin wax baths, a heat chamber and a water blanket, many physicians now favor an extracorporeal heat exchange (blood) circuit when whole body heating is the goal. Patients may be maintained at 41.5° to 42° C. (rectal temperature) for three to four hours without severe compromise of cardiovascular function, although others report elevation of serum transaminases and bilirubin in patients kept at these temperatures for greater than 10 to 40 minutes. Instances of neurologic damage have been reported in association with serum hypophosphatemia, although no significant problems occurred once phosphate levels were maintained. Deaths have also been reported in two patients receiving hyperthermia at 41.5° to 42° C. for 1½ to 2 hours, presumably from massive tumor necrosis, particularly in the liver.

DeMoss, J. L. et al., "Hyperthermia in the Treatment of Cancer," *The Journal of Extra-Corporeal Technology*, Volume 17, No. 1, pp. 37–43, 1985, explains how tumors are vulnerable to heat and that the goal of hyperthermic treatment therapy is to achieve cytotoxic temperatures in the tumor for a sufficient length of time without damaging the surrounding normal tissue. The rate at which blood flows through any given area of tissue determines the amount of heat that may be carried away and therefore is a major determinant of the temperature rise in that tissue. In normal tissue, heat causes vasodilation. In a tumor, the microvasculature is made up of an overabundance of capillary beds which are unable to dilate. Blood flow through the area is thus more sluggish and commensurately unable to dissipate heat applied to the area. The inability to respond to heat by dilation, as normal vasculature would, also subjects the tumor to hypoxia, anaerobic metabolism and local acidosis; these conditions in turn make the tumor tissue more vulnerable to thermal injury.

Other literature addressing the utility of hyperthermia in the treatment of malignancy includes: Sanchez, R., et al., "Overview of Whole Body Hyperthermia Experience at American International Hospital," *Consensus on Hyperthermia for the 1990s*, Plenum Press, New York, pp. 203–208 (1990); Levin, R. D. et al., "Whole Body Hyperthermia Experience in Breast Cancer at American International Hospital," *Consensus on Hyperthermia for the 1990s*, Plenum Press, New York, pp. 387–391 (1990); Perez, C. A. et al., "Randomized Phase III Study Comparing Irradiation and Hyperthermia with Irradiation Alone in Superficial Measurable Tumors," *Am. J. Clin. Oncol.*, vol. 14, no. 2, pp. 133–141 (1991); and others.

Patents relating to methods for the extracorporeal treatment of blood for cancers, viruses and parasites include U.S. Pat. Nos. 2,886,771 to Vincent, No. 3,482,575 to Claff, 4,061,141 to Hyden et al., 4,191,182 to Popovich et al., 4,321,918 to Clark II, 4,322,275 to Jain, 4,381,004 to Babb, 4,479,798 to Parks, 4,540,401 to Marten, 4,563,170 to Aigner, 4,576,143 to Clark III and 4,692,138 to Troutner et al.

There were two reasons for exploring the use of hyperthermia as a treatment for viral-associated neoplasms when such work began a few years ago. First, hyperthermia was known to have caused tumor regression in both animal and in human sarcomas. Studies on the biochemical and physiologic effects of hyperthermia had shown that damage to microvasculature is important for tissue necrosis associated with heat. Second, the human lymphadenopathy associated virus was known to be heat-sensitive. McDougal et al. incubated lymphadenopathy associated virus at temperatures ranging from 37° to 60° C. and found the log kill followed first order kinetics. Thermal inactivation was decreased when the virus was in the lyophilized state compared to the liquid state (10 fold loss in LD50 121 seconds at 56° C. for virus in media versus 32 minutes in lyophilized state). It was also found that lymphadenopathy virus was 40% inactivated after 30 minutes in a 42° C. waterbath, and 100% inactivated after the same time period at 56° C. Thus, hyperthermia can benefit patients suffering from viral infections in two ways. First, the hyperthermia kills malignant cells in the viral-associated neoplasms. Second, the hyperthermia directly inactivates the viruses themselves by denaturing them.

Studies have previously been completed in which whole body hyperthermia, achieved via extracorporeal circulation and thermoregulation, was used to treat Kaposi's Sarcoma associated with human immunodeficiency virus infection. While evaluation of the therapeutic effects of such treatment was the primary purpose of these studies, the simultaneous effects on HIV disease were evaluated by studying immunologic and virologic parameters of HIV infection as well as immunologic parameters related to Kaposi's Sarcoma.

In fact, the use of hyperthermia in acquired immunodeficiency syndrome patients with Kaposi's Sarcoma has received considerable public and media attention. The first two patients upon whom this procedure was performed were patients of the Atlanta pathologist Dr. Kenneth Alonso. Dr. Alonso initiated this experimental use of hyperthermia with Dr. William Logan, Jr., an Atlanta surgeon, as a pilot project to examine the possible use of this technique in the treatment of human immunodeficiency virus-associated diseases. Subsequently, Dr. Alonso requested that the National Institute of Allergy and Infectious Diseases (NIAID) evaluate the study techniques, results and patients.

As reported in O'Malley, S., "Hyperthermia: Perfusion's Answer . . . ?", *Perfusion Life*, January 1991, pp. 6–13, a patient named Carl Crawford experienced a dramatic recovery from head-to-toe skin cancers after being treated with extracorporeal blood heating. (This case study was published in Logan, W. D. et al., "Case Report: Total Body Hyperthermia in the Treatment of Kaposi's Sarcoma . . . ," *Med. Oncol. & Tumor Pharmacother.*, vol. 8, no. 1, pp. 45–47 (1991).) Mr. Crawford had been diagnosed as having Kaposi's Sarcoma incident to human immunodeficiency virus infection, and had been told he had only two to four weeks left to live. Mr. Crawford was the first patient of Drs. Alonso and Logan, who together with perfusionist Joseph A. Guzman heated his blood to 42° C. which, the doctors said, killed the human immunodeficiency virus. Although NIAID discounted Mr. Crawford's recovery due to an alleged error in diagnosis—NIAID maintained that Mr. Crawford never had Kaposi's Sarcoma but had cat-scratch fever instead—six other doctors besides Drs. Alonso and Logan had diagnosed Mr. Crawford's skin lesions as Kaposi's Sarcoma and growing numbers of physicians are convinced that hyperthermia provides a proven antiviral protocol. For example, Dr. Robert S. Jenkins, Medical Director of the Immuno Suppressed Unit at Hollywood Community Hospital, believes that the hyperthermia was responsible for curing Mr. Crawford's Kaposi's Sarcoma lesions.

In a completely separate effort from Drs. Alonso and Logan, Dr. Shawn Hankins, a chiropractor in Port Angeles, Wash., has supported hyperthermia treatments since July, 1987 (as explained in the *Acquired Immunodeficiency Syndrome Treatment News*, Issue No. 104, Jun. 1, 1990, page 2). He points out that human immunodeficiency virus is heat sensitive and, in addition, hyperthermia can cause increased T-cell proliferation, phagocytosis, and increased production of antibodies and interferon. Observations of phenomenon such as the "honeymoon effect" that sometimes follows pneumocystitis (which causes a high fever) also support this conclusion.

Other publications directed generally toward the treating of human immunodeficiency virus with heat include: Weatherburn, H., "Hyperthermia . . . ," *The British Journal of Radiology*, vol. 61, no. 729, pp. 863–864 (1988); Yatvin, M. B., "An Approach . . . Using Hyperthermia and Membrane Modification," *Medical Hypotheses*, vol. 27, pp. 163–165 (1988); and U.S. Pat. No. 4,950,225 to Davidner et al., "Method for Extracorporeal Blood Shear Treatment."

The latter, Davidner et al., discusses the extracorporeal treatment of the blood of a human immunodeficiency virus patient with a) hyperthermia; b) mechanical shear and/or c) irradiation. When hyperthermia is used, the blood is heated to between 41.0° and 42.5° C. (or somewhat higher), and pH is adjusted by oxygenating the blood with an extracorporeal oxygenator and by adding sodium bicarbonate intravenously when necessary. Blood is held under low flow or static conditions, extracorporeally, so that the blood treatment or treatments are (assertedly) maximally successful in ineffectuating the human immunodeficiency virus.

Among the known protocols for heating blood, various difficulties persist, including (as outlined above) elevated serum transaminases and bilirubin, instances of neurologic damage associated with serum hypophosphatemia, risk due to abnormal pH or to abnormal sodium, sodium bicarbonate or potassium levels, and possible death from massive tumor necrosis. Previously attempted treatments of human immunodeficiency virus with hyperthermia have included some measures to maintain normal blood physiology (the sodium bicarbonate addition of Davidner et al., for example) in what can best be characterized as a "shotgun" approach to minimizing hyperthermia side effects. A need therefore remains for a more reliable, simpler and more comprehensive extracorporeal hyperthermia treatment method in which unwanted side effects are reduced or eliminated altogether.

SUMMARY OF THE INVENTION

The present invention is a method for extracorporeal blood treatment which utilizes a hemodialysis machine capable of heating the dialysis fluids to 48° C., a hollow fiber high efficiency hemodialyzer, and a tubular heat exchanger—in addition to various probes and catheters and heated anterior and posterior blankets for the patient—to effect extracorporeal treatment without adverse effect on blood physiology and without the need for general anesthesia. Incorporation of hemodialysis into the blood heating treatment solves at once several problems which plagued prior art hyperthermia protocols: it rectifies any imbalances of sodium, potassium, sodium bicarbonate, or phosphate, and removes any toxins incident to necrosis of any tumors, viral bodies or other tissues. Hyperthermia protocols which include appropriate hemodialysis thus avoid the various serious side effects which complicated—sometimes even to the point of death—the hyperthermia treatments known from the past.

DETAILED DESCRIPTION OF THE INVENTION

The present invention is a method for extracorporeal blood treatment which utilizes a hemodialysis machine capable of heating the dialysis fluids to 48° C., a hollow fiber high efficiency hemodialyzer, and a tubular heat exchanger—in addition to various probes and catheters and heated anterior and posterior blankets for the patient—to effect extracorporeal treatment without adverse effect on blood physiology and without the need for general anesthesia. Incorporation of hemodialysis into the blood heating treatment rectifies any imbalances of sodium, potassium, sodium bicarbonate, or phosphate, and removes any toxins incident to necrosis of any tumors, viral bodies or other tissues.

The technique itself can be summarized as follows. After amnesics and analgesics or other sedation (not general anesthesia) are given to the patient, an Impra double-lumen catheter is placed—by catheter placement techniques known in the art including local anesthesia—in the jugular, subclavian or femoral vein (whichever is most accessible for any given patient). Heparinization is effected only upon initial catheterization at a level of approximately 2.4 mg. per kilogram patient body weight. A heating-cooling mattress is positioned under the patient, and a heating-cooling blanket over the patient, to assist in effecting whole-body hyperthermia. A hemodialyzer capable of increasing the temperature of the dialyzing solution to 48° C. is incorporated in the extracorporeal blood "circuit"; the circuit also contains a hollow-fiber, high flux dialyzer and a heat exchanger for rapid control of the temperature. The desired core body temperature of about 42° C. (41°–42.5° C., more preferably 41.5°–42° C.) is reached in about 40 to 50 minutes. This elevated body temperature is maintained for 2 hours, and cooling is subsequently effected over a period of 20 to 40 minutes. During the procedure, the patient is monitored for pulmonary artery pressure, radial artery pressure and pulmonary artery and bladder temperature. After 2 hours, patient is cooled to between 38° and 39° C. and extracorporeal blood circulation is ended.

More particularly, after placement of the catheter, the blood flows through 1) a hemodialysis machine; 2) a hollow-fiber, high flux dialyzer; 3) a tubular heat exchanger and 4) a stopcock for collecting and/or monitoring the extracorporeal blood, prior to return of circulation through the same catheter. An exemplary hemodialysis machine is the A2008DJ 8E, manufactured by Fresenius, USA. Hollow-fiber, high flux dialyzers are well known in the art, but one among the many available is the F80 dialyzer, also available from Fresenius, USA. A suitable tubular heat exchanger is available from Avecor (A-19-38 Omnitherm Adult Heat Exchanger). Optional additions to the blood circuit include a blood pump upstream of the hemodialysis machine, a temperature probe and/or an air filter. The air filter removes any air emboli which may be circulating in the system. The patient should rest on and be covered by heating/cooling mattresses/blankets to allow the practitioner to augment blood heating with direct body heating, to facilitate the raising of the core body temperature.

All of the above equipment is well known in the art and only minor modifications are required prior to its use in the present process. The hemodialysis machine should be modified to allow the temperature of the dialyzing fluid to be maintained at 48° C., something hemodialysis machines have never heretofore been intended to do. Notwithstanding this, however, modifying a hemodialysis machine to provide controlled heat to the dialyzing fluid is a simple mechanical modification well within the ordinary skill of the art. The tubular heat exchanger is included in the system to confer (or remove) additional heat beyond that provided by the heated dialyzing fluids. Heating/cooling blankets/mattresses and their associated equipment (an entire system of these devices is available, for instance, from Cincinnati Sub-Zero Products, Inc.) may be used without modification.

Because of the patient's natural depletion of carbohydrate and fat stores, these substances should be administered during and/or after treatment to assure that these precursors are adequately available to marginally competent metabolic pathways. Hemodialysis maintains levels of phosphate and calcium during treatment—which levels would otherwise fall as a result of the hyperthermia—especially when acid/bicarbonated water is used as the dialyzing solution. Maintenance of arterial oxygen tensions as high as possible during hyperthermia by use of 100% oxygen for ventilation should satisfy the need to maintain greater than normal blood and tissue oxygen tensions necessitated by hyperthermia-increased oxygen consumption.

Blood flow rates are about 750 ml. per minute when human patients are treated as above.

Fluid electrolyte volume management during the procedure is shown in a table appearing herein as FIG. 1.

Prior to treatment, patients are screened for underlying heart disease; underlying lung disease (including pulmonary Kaposi's Sarcoma if one or more lesions is greater than a certain size); pregnancy; a Karnofsky score of less than 60%; a non-correctable hematocrit of less than 30 ml.; hemoglobin less than 10%; active opportunistic infection; chemotherapy for any type of cancer 3 or 4 weeks previously; bleeding disorders; or Diabetes Mellitus. Any of the foregoing warrants careful consideration of the risks versus the benefits of hyperthermia treatment, since an important consideration in the practice of the present technique is whether the patient can tolerate it. The prehyperthermia evaluation requires a routine history and physical examination, routine laboratory studies, chest x-rays, urinalysis, electrocardiogram and pulmonary function studies. Special studies include P-24 antigen level assay; reverse transcriptase assay; human immunodeficiency virus cultures; lymphocyte quantitative analysis and thyroid profile.

The present improved hyperthermia technique has application in every indication for which hyperthermia was indicated in the past, namely, to combat neoplasms and viral infections. Human clinical studies have already shown that hyperthermia is effective to treat (not necessarily to cure) viral infections including the retroviral infections such as Hepatitus B and human immunodeficiency viruses. That hyperthermia is effective in all these applications has already been established; the present invention inheres in the improvements to the pre-existing hyperthermia methods and the way in which the improvements avoid the side effects ubiquitous in the prior art.

Unlike previously known whole-body hyperthermia techniques, the present protocol is not conducted using general anesthesia per se but is instead conducted using conscious sedation and/or analgesics. An exemplary analgesic is commercially available as Sublimaze (fentanyl citrate, or N-(1-phenethyl-4-piperidyl) propionanilide citrate), a synthetic narcotic analgesic. An exemplary conscious sedation-inducing drug is Propofol, which is a sedative (or hypnotic agent) widely used in outpatient applications. The chemical formula for Propofol is 2,6-diisopropylphenol; the commercial name is Diprivan injection. These drugs are exemplary only, and the invention is not to be considered as limited to these illustrative medications. (However, Versed (midazolam hydrochloride, or 8-chloro-6-(2-fluorophenyl)-1-methyl-4H-imidazol[1,5-a][1,4] benzodiazepine hydrochloride), a short-acting benzodiazepine central nervous system depressant, should NOT be used, and other benzodiazepine derivatives are likewise contraindicated. Midazolam hydrochloride and benzodiazepine derivatives in general are biologically incompatible with hyperthermia: while Versed demonstrates typical pharmacologic activity (including reversibility) during the present procedure, the combination of the hyperthermia with the body biochemistry incident to hyperthermia causes disastrous central nervous system trauma (and possible death) six hours after the procedure is complete.) With the patient conscious, or at most sedated, central nervous system activity can readily be monitored during hyperthermia treatment.

The use of hemodialysis machines, and hollow-fiber, high flux dialyzers, as well as the underlying technology of their manufacture, is well known and well established in the medical arts. The various acid- and bicarbonate-containing dialyzing solutions available are also well known; typical commercially available dialyzing solutions are Centrisol (Cobe) or Renasol (Fresenius). Dialysis technology is itself well understood, and therefore is not being repeated here. For the purpose of the present invention, the incorporation of dialysis into the extracorporeal blood surface is intended to accomplish the same blood "clean-up" as ordinary dialysis of a renally compromised patient would-even though the hyperthermia patient will ordinarily have functional kidneys. The dialysis procedure allows electrolytes to be regulated (sodium, potassium, phosphate, etc. are all kept at appropriate levels in the blood) and in addition any toxins incident to viral or neoplasm damage or death are "filtered out." Accomplishing such a result is well within the skill of those who customarily administer dialysis procedures. The heart of the present invention is not in the details of effecting the hemodialysis, but in the realization that adding such dialysis to extracorporeal hyperthermia overcomes the various serious side effects which plagued known hyperthermia techniques.

Probably, the combination of hemodialysis and extracorporeal heating was never realized in the past because generally only nephrologists consider using hemodialysis at all, and patients for whom extracorporeal blood heating is indicated seldom if ever have the kidney problems that would suggest the incorporation of hemodialysis in a hyperthermia protocol.

The invention may be further illustrated by means of the following examples.

EXAMPLE 1

For ten young sheep (16 weeks old) studied separately, a double lumen catheter is introduced percutaneously in the femoral vein under general anesthesia. A hemodialyzer is used in the extracorporeal circulation system to control the animal's temperature. The temperature of the dialyzing solution is raised to 48° C. The blood circulating from the cannulated vein goes to the hemodialyzer. A heat exchanger is included in the blood circulating system to enable a quick decrease in temperature in the case of emergency. A Blanketrol-type mattress is also used, in conjunction with the heat exchanger. The animal is covered by this mattress so as to enable temperature control on the animal body surface. After the animal is cannulated and the blood circulation through the hemodialyzer is established, the procedure is initiated by effecting moderate blood flows of approximately 450–600 ml./min. Blood temperature is increased until it reaches 42° C. and the blood temperature is maintained at this level for two hours. A Swan-Ganz catheter with a thermometer is also introduced percutaneously in the pulmonary artery for temperature readings and pulmonary pressure monitoring. Bladder temperatures and urinary volume are monitored with a Foley catheter supplied with a temperature probe. Arterial pressure is monitored with an arterial catheter through which blood gases may also be measured. Electrocardiogram monitors are in place. Every thirty minutes, the animal is monitored for arterial blood gas levels; electrolytes; enzymes; and biopsies of central nervous system, lung, liver, kidneys and skeletal muscle.

Cooling is effected two hours after the blood heating begins, and continues until initial temperature is reached. The animal is then sacrificed for autopsy and to correlate the anatomic/pathologic results with the biopsies and other examinations.

EXAMPLE 2

A pre-operative evaluation of a human immunodeficiency virus infected human patient includes: biopsy of any existing Kaposi's Sarcoma lesion; hematic biometry; biochemical profile; electrolytes; antigen P24; reverse transcriptase assay; western blot; human immunodeficiency virus culture; immunologlobin assay; CD4; phospholipase assay; coagulation studies; interferon assay; interleukine 2 assay; interleukine 2 receptor assay; spirometry; and echocardiogram.

Patients (either male or female) are selected for treatment in this study if they are between the ages of 18 and 40, test positive for the human immunodeficiency virus, and have normal or at least 80% normal pulmonary, cardiac, renal and hepatic functions. (Patients are excluded from this study if they exhibit severe immunodepression, extensive tumoral activity in vital organs (lung, liver, etc.), are at cardiac risk or have had radiation of the mediastinum or vital organs.)

The whole-body hyperthermia is effected on each human patient as follows.

After an analgesic (see below) is given to the patient, an Impra double-lumen catheter is placed (under local anesthesia) in the jugular, subclavian or femoral vein (whichever is most accessible for any given patient). Heparinization is effected only upon initial catheterization at a level of approximately 2.4 mg. per kilogram patient body weight. A heating-cooling mattress is positioned under the patient, and a heating-cooling blanket over the patient, to assist in effecting whole-body hyperthermia. A hemodialyzer capable of increasing the temperature of the dialyzing solution to 48° C. is incorporated in the extracorporeal blood "circuit"; the circuit also contains a hollow-fiber, high flux dialyzer and a heat exchanger for rapid control of the temperature. The desired core body temperature of about 42° C. is reached in about 40 to 50 minutes of extracorporeal blood heating. This elevated body temperature is maintained for 2 hours, and cooling is subsequently effected over a period of 20 to 40 minutes. During the procedure, the patient is monitored for pulmonary artery pressure, radial artery pressure and pulmonary artery and bladder temperature, in addition to core temperature. These values are monitored with temperature probes, catheters and probes known in the art. After 2 hours, the patient is cooled to between 38 ° and 39° C. and extracorporeal blood circulation is ended.

Carbohydrates and fats are administered during and/or after treatment to assure that these precursors are adequately available to marginally competent metabolic pathways. Hemodialysis maintains levels of phosphate and calcium during treatment, which levels would otherwise fall as a result of the hyperthermia, especially when bicarbonated water used as the dialyzing solution. Maintenance of arterial oxygen tensions as high as possible during hyperthermia by use of 100% oxygen for ventilation satisfies the need to maintain greater than normal blood and tissue oxygen tensions necessitated by hyperthermia-increased oxygen consumption.

The analgesic used is Sublimaze (fentanyl citrate, or N-(1-phenethyl-4-piperidyl) propionanilide citrate), a synthetic narcotic analgesic. Coadministration of benzodiazepine derivatives is strictly avoided.

The pre-operative evaluations listed above are repeated 7, 14, 21 and 28 days after the following hyperthermia treatment is effected.

Although the invention has been described with particularity above, it is to be limited only insofar as is set forth in the following claims.

We claim:

1. A method for the extracorporeal heating of blood in a human in which extracorporeal hyperthermia is indicated, comprising the steps of:
   catheterizing a blood vessel of a patient and creating an extracorporeal blood circuit;
   heating at least some of the blood in the extracorporeal blood circuit; and
   subjecting at least some of the blood in the extracoporeal blood circuit to hemodialysis, wherein said heating step further comprises heating at least some of the blood in the extracorporeal blood circuit by elevating the temperature of a dialyzing solution used in the hemodialysis step to about 48° C.

2. The method according to claim 1 wherein said heating step further comprises heating all of the blood in the extracorporeal blood circuit so as to raise the core temperature of said patient to approximately 41.5°–42° C.

3. The method according to claim 2 wherein said extracorporeal blood circuit includes a tubular heat exchanger.

4. The method according to claim 3 wherein said extracorporeal blood circuit includes a stopcock.

5. The method according to claim 4 wherein said hemodialysis is effected by means of a hollow-fiber, high flux dialyzer.

6. The method according to claim 5 wherein said heating step further includes heating the body of said patient with a heated mattress.

7. The method according to claim 6 wherein said heating step further includes heating the body of said patient with a heated blanket.

8. The method according to claim 7 wherein said extracorporeal blood circuit is pumped by means of a pump upstream of a hemodialysis machine and its associated dialyzer.

9. The method according to claim 8 wherein an air filter is positioned in line with said dialyzer and said air filter removes any air emboli which may be circulating in the system.

10. A method for the extracorporeal heating of blood in an animal in which extracorporeal hyperthermia is indicated, comprising the steps of:
    catheterizing a blood vessel of an animal and creating an extracorporeal blood circuit;
    heating at least some of the blood in the extracorporeal blood circuit; and
    subjecting at least some of the blood in the extracorporeal blood circuit to hemodialysis, wherein said heating step further comprises heating at least some of the blood in the extracorporeal blood circuit by elevating the temperature of a dialyzing solution used in the hemodialysis step to about 48° C.

11. The method according to claim 10 wherein said heating step further comprises heating all of the blood in the extracorporeal blood circuit so as to raise the core temperature of said animal to approximately 41.5°–42° C.

12. The method according to claim 11 wherein said extracorporeal blood circuit includes a tubular heat exchanger.

13. The method according to claim 12 wherein said extracorporeal blood circuit includes a stopcock.

14. The method according to claim 13 wherein said hemodialysis is effected by means of a hollow-fiber, high flux dialyzer.

15. The method according to claim 14 wherein said heating step further includes heating the body of said animal with a heated mattress.

16. The method according to claim 15 wherein said heating step further includes heating the body of said animal with a heated blanket.

17. The method according to claim 16 wherein said extracorporeal blood circuit is pumped by means of a pump upstream of a hemodialysis machine and its associated dialyzer.

18. The method according to claim 17 wherein an air filter is positioned in line with said dialyzer and said air filter removes any air emboli which may be circulating in the system.

* * * * *